(12) United States Patent
Lambert et al.

(10) Patent No.: US 8,299,209 B2
(45) Date of Patent: Oct. 30, 2012

(54) PHARMACEUTICAL COMPOSITION COMPRISING CYCLIC SOMATOSTATIN ANALOGUES

(75) Inventors: Olivier Lambert, Spechbach-le-Haut (FR); Katrin Moser, Brookline, MA (US)

(73) Assignee: Novartis AG, Basel (CH)

( * ) Notice: Subject to any disclaimer, the term of this patent is extended or adjusted under 35 U.S.C. 154(b) by 552 days.

(21) Appl. No.: 12/359,527

(22) Filed: Jan. 26, 2009

(65) Prior Publication Data

US 2009/0137462 A1    May 28, 2009

Related U.S. Application Data

(63) Continuation of application No. 10/560,751, filed as application No. PCT/EP2004/006794 on Jun. 23, 2004, now abandoned.

(30) Foreign Application Priority Data

Jun. 24, 2003  (GB) .................................. 0314695.8
Oct. 30, 2004  (GB) .................................. 0325388.7

(51) Int. Cl.
*C07K 14/00* (2006.01)
*C07K 14/655* (2006.01)
*C07K 11/02* (2006.01)

(52) U.S. Cl. ........................................ 530/311; 530/317
(58) Field of Classification Search ........................ None
See application file for complete search history.

(56) References Cited

U.S. PATENT DOCUMENTS

| 4,328,214 A | * | 5/1982 | Rink et al. ..................... 514/7.1 |
| 4,603,120 A | | 7/1986 | Kamber |
| 4,612,366 A | | 9/1986 | Nutt |
| 5,059,587 A | | 10/1991 | Yamamoto et al. |
| 5,616,587 A | | 4/1997 | Francois et al. |
| 5,639,480 A | | 6/1997 | Bodmer et al. |
| 2003/0044463 A1 | * | 3/2003 | Deghenghi et al. ........... 424/468 |
| 2005/0014686 A1 | | 1/2005 | Albert et al. |

FOREIGN PATENT DOCUMENTS

| EP | 0302772 | 2/1989 |
| EP | 1153615 | 11/2001 |
| JP | 2000710 | 8/1997 |
| WO | 94 00489 | 1/1994 |
| WO | 95 00553 | 1/1995 |
| WO | 97 01579 | 1/1997 |
| WO | 02 10192 | 2/2002 |

OTHER PUBLICATIONS

Crow JM, Cancer Drugs for the Next Decade Unveiled from www.rsc.org/chemistryworld/Issues/2008/January/CancerDrugsNextDecadeUnveiled..., pp. 1-2. Nov. 21, 2007.*
Stalla GK, et al: "Octreotide exerts different effects invivo and in vitro in Cushing's disease", European Journal of Endocrinology 1994, 130:125-31.
Reubi et al., "A new peptidic somatostatin agonist with high affinity to all five somatostatin receptors," European Journal of Pharmacology, vol. 456, pp. 45-49 (2002).

* cited by examiner

*Primary Examiner* — Julie Ha
(74) *Attorney, Agent, or Firm* — Stephen Johnson; Greg Houghton

(57) ABSTRACT

Pharmaceutical compositions comprising a somastatin analogue in the form of a liquid formulation for parenteral administration are disclosed.

5 Claims, No Drawings

PHARMACEUTICAL COMPOSITION COMPRISING CYCLIC SOMATOSTATIN ANALOGUES

This is a continuation of application Ser. No. 10/560,751 filed on Dec. 14, 2005, the entire disclosure of which is hereby incorporated by reference.

The present invention relates to parenteral pharmaceutical compositions comprising a somatostatin analogue and to novel somatostatin analogues.

Somatostatin is a tetradecapeptide having the structure

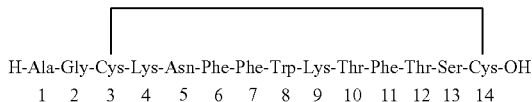

Since the isolation and characterization of somatostatin, an extensive search for more potent and more stable analogues has continued.

Somatostatin analogues have been described e.g. in WO 97/25977. Said somatostatin analogues comprise the amino acid sequence of formula I

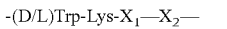

wherein $X_1$ is a radical of formula (a) or (b)

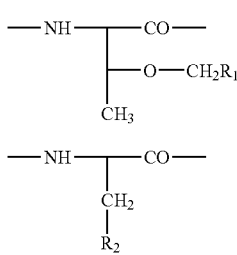

wherein $R_1$ is optionally substituted phenyl,
$R_2$ is $-Z_1-CH_2R_1$, $-CH_2-CO-O-CH_2-R_1$,

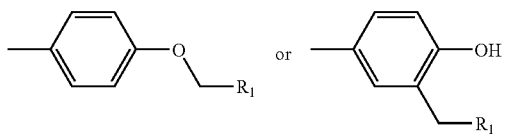

wherein $Z_1$ is O or S, and
$X_2$ is an α-amino acid having an aromatic residue on the $C_α$ side chain, or an amino acid unit selected from Dab, Dpr, Dpm, His, (Bzl)HyPro, thienyl-Ala, cyclohexyl-Ala and t-butyl-Ala, the residue Lys of said sequence corresponding to the residue $Lys^9$ of the native somatostatin-14.

By somatostatin analogue as used herein is meant a straight-chain or cyclic peptide derived from that of the naturally occurring somatostatin-14, comprising the sequence of formula I and wherein additionally one or more amino acid units have been omitted and/or replaced by one or more other amino acid radical(s) and/or wherein one or more functional groups have been replaced by one or more other functional groups and/or one or more groups have been replaced by one or several other isosteric groups. In general the term covers all modified derivatives of the native somatostatin-14 comprising the above sequence of formula I which have binding affinity in the nM range to at least one somatostatin receptor subtype as defined hereinafter.

Preferred are somatostatin analogues in which the residues at positions 8 through 11 of the somatostatin-14 are represented by the sequence of formula I as defined above.

More preferred are somatostatin analogues as disclosed above comprising a hexapeptide unit, the residues at positions 3 through 6 of said hexapeptide unit comprising the sequence of formula I. Even more preferably the residues at positions 1 and 2 of the hexapeptide unit of the somatostatin hexapeptide may be any of those as known in the art, e.g. as disclosed by A. S. Dutta in Small Peptides, Vol. 19, 292-354, Elsevier, 1993, or as substituents for, $Phe^6$ and/or $Phe^7$ of somatostatin-14.

Even more preferred are cyclic somatostatin hexapeptides, e.g. cyclic somatostatin hexapeptides comprising a hexapeptide unit numbered from 1 to 6, the residues at positions 3 through 6 of said hexapeptide unit having the amino sequence of formula I as indicated above, e.g. a compound of formula Ia

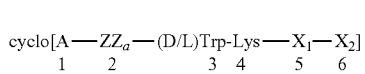

wherein $X_1$ and $X_2$ are as defined above,
A is a divalent residue selected from Pro,

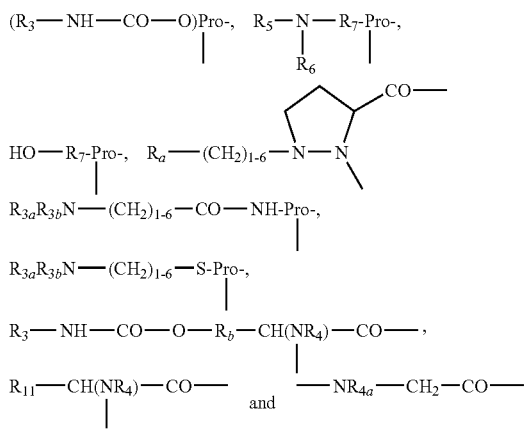

wherein $R_3$ is $NR_8R_9-C_{2-6}$alkylene, guanidino-$C_{2-6}$alkylene or $C_{2-6}$alkylene-COOH, $R_{3a}$ is H, $C_{1-4}$alkyl or has independently one of the significances given for $R_3$, $R_{3b}$ is H or $C_{1-4}$alkyl, $R_a$ is OH or $NR_5R_6$, $R_b$ is $-(CH_2)_{1-3}-$ or $-CH(CH_3)-$, $R_4$ is H or $CH_3$, $R_{4a}$ is optionally ring-substituted benzyl, each of $R_5$ and $R_6$ independently is H, $C_{1-4}$alkyl, ω-amino-$C_{1-4}$alkylene, ω-hydroxy-$C_{1-4}$alkylene or acyl, $R_7$ is a direct bond or $C_{1-6}$alkylene, each of $R_8$ and $R_9$ independently is H, $C_{1-4}$alkyl, ω-hydroxy-$C_{2-4}$alkylene, acyl or $CH_2OH-(CHOH)_c-CH_2-$ wherein c is 0, 1, 2, 3 or 4, or $R_8$ and $R_9$ form together with the nitrogen atom to which they are attached a heterocyclic group which may comprise a further heteroatom, and $R_{11}$ is optionally ring-substituted benzyl, $-(CH_2)_{1-3}-OH$, $CH_3-CH(OH)-$ or $-(CH_2)_{1-5}-NR_5R_6$, and $ZZ_a$ is a natural or unnatural α-amino acid unit.

Particularly preferred are compounds of formula II

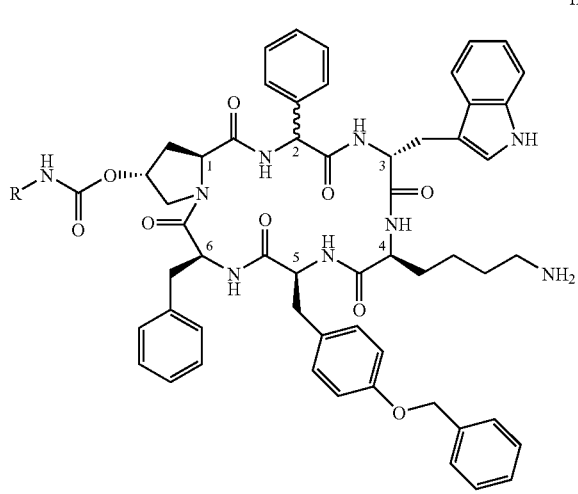

II wherein the configuration at C-2 is (R) or (S) or a mixture thereof, and
wherein R is $NR_1R_2$—$C_{2-6}$alkylene or guanidine-$C_{2-6}$alkylene, and each of $R_1$ and $R_2$ independently is H or $C_{1-4}$alkyl, in free form, in salt form or protected form.

Preferably R is $NR_1R_2$—$C_{2-6}$alkylene. Preferred compounds of formula II are the compounds wherein R is 2-amino-ethyl, namely cyclo[{4-($NH_2$—$C_2H_4$—NH—CO—O—)Pro}-Phg-DTrp-Lys-Tyr(4-Bzl)-Phe] (referred herein to as Compound A) and cyclo[{4-($NH_2$—$C_2H_4$—NH—CO—O—)Pro}-DPhg-DTrp-Lys-Tyr(4-Bzl)-Phe], in free form, salt form or protected form. Phg means —HN—CH($C_6H_5$)—CO— and Bzl means benzyl.

These compounds in free form, salt form or protected form are referred to hereinafter as "compounds of the invention".

Due to proteolytic degradation of the somatostatin analogues of the present invention, systemic delivery, e.g. parenteral administration, is highly desirable. However, parenteral administration may be very painful at the site of administration, especially in repeated administration.

It has now been found that parenteral compositions comprising a compound of the invention, and tartaric acid show particularly interesting properties, e.g. good tolerability and high stability.

A compound of the invention in protected form corresponds to a somatostatin analogue wherein at least one of the amino groups is protected and which by deprotection leads to a compound of formula II, preferably physiologically removable. Suitable amino protecting groups are e.g. as disclosed in "Protective Groups in Organic Synthesis", T. W. Greene, J. Wiley & Sons NY (1981), 219-287, the contents of which being incorporated herein by reference. Example of such an amino protecting group is acetyl.

A compound of the invention may exist e.g. in free or salt form. Salts include acid addition salts with e.g. inorganic acids, polymeric acids or organic acids, for example with hydrochloric acid, acetic acid, lactic acid, aspartic acid, benzoic acid, succinic acid or pamoic acid. Acid addition salts may exist as mono- or divalent salts, e.g. depending whether 1 or 2 acid equivalents are added. Preferred salts are the lactate, aspartate, benzoate, succinate and pamoate including mono- and di-salts, more preferably the aspartate di-salt and the pamoate monosalt.

The compounds of the invention may be prepared in accordance with conventional methods.

In a first aspect, the present invention provides a parenteral composition comprising a compound of the invention and tartaric acid.

According to the invention, typically the concentration of the compound of the invention in the composition of the invention is from about 0.05 to about 1 mg per ml composition, particularly 0.1 to 1 mg/ml.

Conveniently, the ratio of the compound of the invention (amount corresponding to free form) to tartaric acid is about 0.001 to about 2 weight in weight, preferably about 0.05 to about 0.6.

The amount of the compound of the invention in the composition of the invention is from about 0.005% to about 0.1% based on a total weight of the formulation.

Preferably, the tartaric acid is in fine crystalline form. More preferably, crystalline D(−) or L(+) tartaric acid is used. The amount of tartaric acid is preferably from about 0.01% to about 1.5% w/w of the formulation, preferably about 0.01% to about 0.3%, more preferably about 0.15%. Preferably, the molarity of tartaric acid in the final composition is about 10 mM.

In accordance with the present invention, in addition to the tartaric acid and a compound of the invention, the pharmaceutical composition preferably comprises also a basic component selected and added to the composition in such a way that the pH of the tartaric acid buffered pharmaceutical composition is adjusted to a pH of about 4 to about 4.5, preferably about 4.2.

Preferably, the basic component is a base, e.g. sodium hydroxide or potassium hydroxide, or a basic salt e.g. sodium hydrogen carbonate, sodium carbonate, potassium hydrogen carbonate, or potassium carbonate. Preferably, the basic component is added in such an amount that the resulting pharmaceutical composition has a pH buffered as indicated above.

Preferably, the pharmaceutical composition of the invention is water based.

The compositions of the invention may further comprise a tonicity agent such as mannitol, sodium chloride, glucose, dextrose, sucrose, or glycerins. Preferably, the tonicity agent is mannitol.

The amount of tonicity agent is chosen to adjust the isotonicity of the composition of the invention, e.g. mannitol preferably may be from about 1% to about 5% by weight of the composition, preferably about 4.95%. Conveniently, mannitol is present in a ratio mannitol to tartaric acid of about 20 to about 40, preferably about 33.

The compositions of the invention may contain additional excipients commonly employed in parenteral compositions in order to provide the required stability and therapeutic efficacy. Excipients may include e.g. an antioxidant or a preserving agent.

Antioxidants may be employed to protect the active agent from oxidative degradation particularly under the accelerated conditions of thermal sterilisation. Antioxidants may be selected from any of those compounds known in the art. Similarly, the amount of antioxidant employed can be determined using routine experimentation. Preferably, the compositions of the invention do not contain an antioxidant.

A preserving agent, e.g. phenol, may preferably be added to the composition when it is formulated as multidose vials, cartridges or syringes. Preferably, the compositions of the invention do not contain a preserving agent.

Reference is made to the extensive literature on the subject for these and other excipients and procedures mentioned herein, see in particular Handbook of Pharmaceutical Excipients, Second Edition, edited by Ainley Wade and Paul J. Weller, American Pharmaceutical Association, Washington, USA and Pharmaceutical Press, London; and Lexikon der Hilfsstoffe für Pharmazie, Kosmetik and angrenzende Gebiete edited by H. P. Fiedler, 4th Edition, Editio Cantor, Aulendorf and earlier editions which are incorporated herein by reference.

Preferably, the composition of the invention contains as active ingredient only compound of the invention, e.g. a compound of formula II, e.g. Compound A.

Procedures which may be used to prepare the compositions of the invention may be conventional or known in the art or based on such procedures e.g. those described in L. Lachman et al. The Theory and Practice of Industrial Pharmacy, 3rd Ed, 1986, H. Sucker et al, Pharmazeutische Technologie, Thieme, 1991, Hager's Handbuch der pharmazeutischen Praxis, 4th Ed. (Springer Verlag, 1971) and Remington's Pharmaceutical Sciences, 13th Ed., (Mack Publ., Co., 1970) or later editions.

Typically, the compound of the invention, the tartaric acid and optionally the other ingredients as mentioned in the desired amount are dissolved in an aqueous solvent, preferentially in water for injection, and the pH is adjusted with the base. The resulting solution may then be diluted with water to make it up to the final desired volume. The resulting solution may be filtered through a sterile filter, e.g. a MILLIPAK® filter. Preferably, during above preparation oxygen (air) is displaced from contact with the solution of the compound of the invention. This is usually carried out by purging with, e.g. nitrogen, a container holding the solution. The pharmaceutical composition may be packed under carbon dioxide or other inert gas to prevent degradation, preferably under carbon dioxide, e.g. charged into vials, e.g. glass vials, ampoules, e.g. glass ampoules, or syringes, e.g. prefilled syringes, and steam or heat sterilized.

The solution may be freeze-dried by a conventional method under aseptic conditions to give a powder for injection which may be used to reconstitute the desired solution for parenteral administration shortly before administration by mixing the powder with the desired amount of solvent e.g. with water for injection.

Alternatively, the present invention provides in another aspect a composition for parenteral administration buffered at a pH of about 4 to about 4.5, preferably about 4.2, and comprising as active ingredient compound A or a pharmaceutically acceptable salt thereof, e.g. a lactate, mono- or di-aspartate, succinate, preferably a aspartate di-salt.

These compositions may comprise the same components as described above for compositions comprising tartaric acid wherein the tartaric acid/tartrate is replaced by another buffer such as acetate/acetic acid, lactate/lactic acid, and Glycin/HCl.

The compositions of the invention are useful a) for the prevention or treatment of disorders with an aetiology comprising or associated with excess GH-secretion and/or excess of IGF-1 e.g. in the treatment of acromegaly as well as in the treatment of type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity, b) in the treatment of enterocutaneous and pancreaticocutaneous fistula, irritable bowel syndrom, inflammatory diseases, e.g. Grave's Disease, inflammatory bowel disease, psoriasis or rheumatoid arthritis, polycystic kidney disease, dumping syndrom, watery diarrhea syndrom, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding, c) for the prevention or treatment of angiogenesis, inflammatory disorders as indicated above including inflammatory eye diseases, macular edema, e.g. cystoid macular edema, idiopathic cystoid macular edema, exudative age-related macular degeneration, choroidal neovascularization related disorders and proliferative retinopathy, d) for preventing or combating graft vessel diseases, e.g. allo- or xenotransplant vasculo-pathies, e.g. graft vessel atherosclerosis, e.g. in a transplant of organ, e.g. heart, lung, combined heart-lung, liver, kidney or pancreatic transplants, or for preventing or treating vein graft stenosis, restenosis and/or vascular occlusion following vascular injury, e.g. caused by catherization procedures or vascular scraping procedures such as percutaneous transluminal angioplasty, laser treatment or other invasive procedures which disrupt the integrity of the vascular intima or endothelium, e) for treating somatostatin receptor expressing or accumulating tumors such as pituitary tumors, e.g. Cushing's Disease, gastro-enteropancreatic, carcinoids, central nervous system, breast, prostatic (including advanced hormone-refractory prostate cancer), ovarian or colonic tumors, small cell lung cancer, malignant bowel obstruction, paragangliomas, kidney cancer, skin cancer, neuroblastomas, pheochromocytomas, medullary thyroid carcinomas, myelomas, lymphomas, Hodgkins and non-Hodgkins lymphomas, bone tumours and metastases thereof as well as autoimmune or inflammatory disorders, e.g. rheumatoid arthritis, Graves disease or other inflammatory eye diseases.

Preferably, the compositions of the invention are useful in the treatment of acromegaly and cancer, e.g. Cushing's Disease.

The activity and characteristics of the compositions of the invention may be indicated in standard clinical or animal tests.

Appropriate dosage of the composition of the invention will of course vary, e.g. depending on the condition to be treated (for example the disease type or the nature of resistance), the drug used, the effect desired and the mode of administration.

When given continuously, an effective amount of drug may be given in two or three doses spread over time such as by parenteral administration, e.g. intravenous drip, intramuscular or subcutaneous injection(s), or subcutaneous infusion, e.g. continuous subcutaneous infusion, preferably subcutaneous injection or infusion, with the total daily dose being spread across the portion or the entire administration period. When given by subcutaneous injection, it is most preferably administered from 3 times per week up to 3 times a day, preferably twice a week up to once or twice daily. A compound of the invention may also be administered in the form of e.g. a subcutaneous bolus injection.

The composition of the invention preferably is suitable for subcutaneous administration.

After injection, the composition of the invention is locally well tolerated. Particularly, the parenteral administration of a composition of the invention, e.g. subcutaneous injection, leads to mild to no burning sensation at the injection site.

In addition to the good local tolerance after injection, the composition of the invention exhibits good stability characteristics. For example, less than 2.5% of degradation products were found after 4 weeks storage at 60° C. For example, if stored with light protection at 2° C. to 8° C., the compositions of the invention are stable over 24 months. Particularly good stability may be observed with the diaspartate salt of Compound A.

In general, satisfactory results are obtained on administration, e.g. subcutaneous administration, at dosages on the order of from about 0.01 to about 1.2 mg, preferably from about 0.1 to about 0.6 mg of the compound of the invention per injection or about 0.001 to about 0.009 mg per kg animal body weight per day, administered once or in divided doses up to 4 times per day. Suitable daily dosages for patients are thus in the order of about 0.1 mg to about 0.6 mg of a compound of the invention, e.g. a compound of formula II, e.g. Compound A.

The following Examples serve to illustrate the compositions of the invention.

EXAMPLES 1 to 7

Tartaric acid and mannitol are dissolved in water for injection, while the solution is purged with nitrogen. Then diaspartate salt of compound A is added, the solution is adjusted with sodium hydroxide to pH 4.20 and water for injection up to 1.0 ml is added. Under aseptic conditions, the solution is filtered through a MILLIPAK-200® sterile filter with a pore size ≦0.22 μm, filled into ampoules and sterilized by autoclaving.

In yet another aspect, the present invention provides novel compounds of formula III

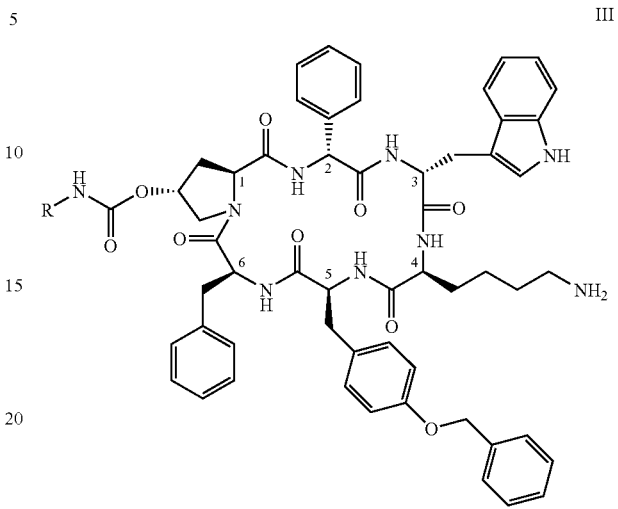

wherein R is $NR_1R_2$—$C_{2-6}$alkylene or guanidine-$C_{2-6}$alkylene, and
each of $R_1$ and $R_2$ independently is H or $C_{1-4}$alkyl,
in free form, in salt form or complex form, or in protected form.

Preferably R is $NR_1R_2$—$C_{2-6}$alkylene. A preferred compound of formula III is the compound wherein R is 2-aminoethyl, also called cyclo[{4-($NH_2$—$C_2H_4$—NH—CO—O—)Pro}-DPhg-DTrp-Lys-Tyr(4-Bzl)-Phe], and referred herein to as Compound B,
in free form, in salt or complex form or in protected form. Phg and Bzl are as defined above.

These compounds in free form, in salt form or complex form, or in protected form are referred hereinafter as "novel compounds of the invention".

A compound of formula II, e.g. Compound B, in protected form corresponds to above molecule wherein at least one of the amino groups is protected and which by deprotection leads to a compound of formula IIII, preferably physiologically removable. Suitable amino protecting groups are e.g. as disclosed in "Protective Groups in Organic Synthesis", T. W. Greene, J. Wiley & Sons NY (1981), 219-287, the contents of which being incorporated herein by reference. Example of such an amino protecting group is acetyl.

|  | Ex 1 | Ex 2 | Ex 3 | Ex 4 |
|---|---|---|---|---|
| diaspartate salt of Compound A | 0.251 | 0.315 | 0.376 | 0.472 |
| (corresponding amount of Compound A) | (0.200) | (0.251) | (0.300) | (0.376) |
| tartaric acid crystalline | 1.501 | 1.501 | 1.501 | 1.501 |
| mannitol | 49.500 | 49.500 | 49.500 | 49.500 |
| sodium hydroxide 1N for injection | ad pH 4.20 | ad pH 4.20 | ad pH 4.20 | ad pH 4.20 |
| water for injection | ad 1 ml | ad 1 ml | ad 1 ml | ad 1 ml |

|  | Ex 5 | Ex 6 | Ex 7 |
|---|---|---|---|
| diaspartate salt of Compound A | 0.752 | 0.786 | 1.129 |
| (corresponding amount of Compound A) | (0.600) | (0.627) | (0.900) |
| tartaric acid crystalline | 1.501 | 1.501 | 1.501 |
| mannitol | 49.500 | 49.500 | 49.500 |
| sodium hydroxide 1N for injection | ad pH 4.20 | ad pH 4.20 | ad pH 4.20 |
| water for injection | ad 1 ml | ad 1 ml | ad 1 ml |

When a compound of formula III, e.g. Compound B, exists in complex form, it may conveniently be a compound of formula III bearing a chelating group on the side chain amino group of Pro and complexed with a detectable or radiotherapeutic element. Compound B bearing a chelating group is referred to hereinto as conjugated Compound B.

Examples of chelating groups include e.g. those derived from poly-aminopolycarboxylic acids or anhydrides, e.g. those derived from non cyclic ligands e.g. diethylene triamine pentaacetic acid (DTPA), ethylene glycol-0,0'-bis(2-aminoethyl)-N,N,N',N'-tetraacetic acid (EGTA), N,N'-bis(hydroxybenzyl)ethylenediamine-N,N'-diacetic acid (HBED) and triethylene-tetramine hexaacetic acid (TTHA), dose derived from substituted DTPA, e.g. p-isothio-cyanato-benzyl-DTPA, those derived from macrocyclic ligands, e.g. 1,4,7,10-tetra-azacyclododecane-N,N',N'',N'''-tetraacetic acid (DOTA), 1,4,8,11-tetraazacyclotetradecane-N,N',N'',N'''-tetraacetic acid (TETA), or 1,4,7,10-tetraazacyclotridecane-N,N',N'',N'''-tetraacetic acid (TITRA).

The chelating group may be attached either directly or through a spacer to the side chain amino group of Pro. Suitable spacers include those known in the art, e.g. as disclosed in GB-A-2,225,579, for example the divalent residue of an amino-carboxylic acid, for example β-Ala or a divalent residue derived from 6-amino-caproic acid.

Preferred chelating groups are those derived from DTPA, DOTA or TETA. Chelating groups derived from DTPA or DOTA are most preferred.

By detectable element is meant any element, preferably a metal ion which exhibits a property detectable in vivo diagnostic techniques, e.g. a metal ion which emits a detectable radiation or a metal ion which is capable of influencing NMR relaxation properties. By radiotherapeutic element is meant any element which emits a radiation having a beneficial effect on the conditions to be treated.

Suitable elements include for example heavy elements or rare earth ions, e.g. as used in CAT scanning (Computer axial tomography), paramagnetic ions, e.g. $Gd^{3+}$, $Fe^{3+}$, $Mn^{2+}$ and $Cr^{2+}$, fluorescent metal ions, e.g. $Eu^{3+}$, and radionuclides, e.g. a radiolanthanide, particularly a γ-emitting radionuclide, β-emitting radionuclide, α-emitting radionuclide, Auger-e⁻-emitting radionuclide or a positron-emitting radionuclide e.g. $^{68}Ga$, $^{18}F$ or $^{86}Y$.

Suitable γ-emitting radionuclides include those which are useful in diagnostic techniques. The γ-emitting radionuclides advantageously have a half-life of from 1 hour to 40 days, preferably from 5 hours to 4 days, more preferably from 12 hours to 3 days. Examples are radioisotopes from Gallium, Indium, Technetium, Ytterbium, Rhenium, Terbium, Lutetium, Thallium and Samarium e.g. $^{67}Ga$, $^{111}In$, $^{99m}Tc$, $^{161}Tb$, $^{169}Yb$, $^{186}Re$ or $^{177}Lu$.

Suitable β-emitting radionuclides include those which are useful in radiotherapeutic applications, for example $^{90}Y$, $^{67}CU$, $^{186}Re$, $^{168}Re$, $^{169}Er$, $^{121}Sn$, $^{127}Te$, $^{177}Lu$, $^{143}Pr$, $^{198}Au$, $^{109}Pd$, $^{165}Dy$, $^{142}Pr$ or $^{153}Sm$.

Suitable α-emitting radionuclides are those which are used in therapeutic treatments, e.g. $^{211}At$, $^{212}Bi$ or $^{201}Tl$.

Compounds of formula III, e.g. Compound B, may exist e.g. in free or salt form. Salts include acid addition salts with e.g. inorganic acids, polymeric acids or organic acids, for example with hydrochloric acid, acetic acid, lactic acid, aspartic acid, benzoic acid, succinic acid or pamoic acid. Acid addition salts may exist as mono- or divalent salts, e.g. depending whether 1 or 2 acid equivalents are added to the Compound B in free base form. Preferred salts are the lactate, aspartate, benzoate, succinate and pamoate including mono- and di-salts, more preferably the aspartate di-salt and the pamoate monosalt.

The conjugated compounds of formula III, e.g. conjugated Compound B, may additionally exist in salt forms obtainable with the carboxylic acid groups when present in the chelating group, e.g. alkali metal salts such as sodium or potassium, or substituted or unsubstituted ammonium salts.

The present invention also includes a process for the production of a compound of formula III, e.g. Compound B. It may be produced in analogy to known methods, for example:
a) cyclising a linear peptide in protected, polymer-bound or unprotected form in such a way that a compound of formula III, e.g. Compound B, is obtained and then optionally removing the protecting group(s),
b) to produce a conjugated compound of formula III, e.g. conjugated Compound B, linking together a chelating group and the compound of formula III, e.g. Compound B, in protected or unprotected form and then optionally removing the protecting group, and recovering the compound of formula III, e.g. Compound B, or a conjugated compound of formula III, e.g. conjugated Compound B thus obtained, in free form, in salt form or optionally complexed with a detectable or radiotherapeutic element.

It is generally not critical which amino acid is selected to be at the C-terminal position to start the peptide chain since the linear peptide will be cyclized, provided only that the sequence of amino acids in the linear peptide corresponds to that in the desired compound of formula III, e.g. Compound B. However there may be other factors which may prefer one starting amino acid over another. When a compound of formula III, e.g. Compound B, is prepared by solid phase synthesis, the first amino-acid is preferably attached to the resin, e.g. a commercially available polystyrene-based resin, through a suitable linker, e.g. a linker which is cleavable under mild conditions to keep the side chain protection intact, e.g. SASRIN or an optionally substituted trityl based linker, for example 4-(hydroxy-diphenyl-methyl)-benzoic acid wherein one the phenyl groups may optionally be substituted e.g. by Cl. The building up of the desired peptide chain may be effected in conventionnal manner, e.g. using amino-acid units wherein the terminal amino group is Fmoc-protected, the side chain amino groups where present being protected with a different amino protecting group, e.g. Boc or CBO. Preferably the linear peptide is cyclized in such a way to produce a bond between Tyr(4-Bzl)-OH and Phe, e.g. Phe-{4-($NHR_1$—$C_2H_4$—NH—CO—O—)Pro}-DPhg-DTrp($R_2$)-Lys(ε-$NHR_3$)-Tyr(4-Bzl)-OH or a functional derivative thereof, wherein each of $R_1$, $R_2$ and $R_3$ is an amino protecting group. The cyclisation step a) may conveniently be performed according to known method, e.g. via an azide, an active ester, a mixed anhydride or a carbodiimide. Thereafter the protecting groups are removed, e.g. by cleavage e.g. with trifluoroacetic or by hydrogenation.

The cyclisation of the peptide may also be performed directly on the solid support, the first amino acid being in a Nα- and C-terminal protected form and attached through a side chain, e.g. ε-amino function of Lys or by backbone anchoring. The linear sequence is then synthesized following standard solid phase synthesis (SPPS) procedures. After cleavage of the C-terminal protection the peptide is cyclized e.g. as described above. Thereafter the cyclic peptide is cleaved from the resin and deprotected.

If desired, the lateral chain present on Pro may be introduced on the amino acid prior to or after the peptide cyclisation step a). Thus, Pro as a starting amino-acid or a starting linear or cyclic peptide wherein in each case Pro is ring-substituted by OH, may be converted to provide a compound of formula III, e.g. Compound B, or the desired Pro unit or the corresponding linear peptide, respectively, wherein Pro is substituted by $NHR_1$—$C_2H_4$—NH—CO—O—.

The complexation of a conjugated compound of formula III, e.g. conjugated Compound B, may be performed by reacting the conjugated compound of formula III, e.g. the conjugated Compound B, with a corresponding detectable or radiotherapeutic element yielding compound, e.g. a metal salt, preferably a water-soluble salt. The reaction may be carried out by analogy with known methods, e.g. as disclosed in Perrin, Organic Ligand, Chemical Data Series 22. NY Pergamon Press (1982); in Krejcarit and Tucker, Biophys. Biochem. Res. Com. 77: 581 (1977) and in Wagner and Welch, J. Nucl. Med. 20: 428 (1979).

The following examples are illustrative of the novel compounds of the invention of formula III. All temperatures are in ° C.
Abbreviations:

| | |
|---|---|
| AcOH = | acetic acid |
| Boc = | tert.-butoxy-carbonyl |
| Bzl = | benzyl |
| CBO = | carbobenzoxy |
| DIPCI = | N,N'-diisopropylcarbodiimide |
| DIPEA = | diisopropylethylamine |
| DMF = | dimethylformamide |
| DPPA = | diphenylphosphorylazide |
| Fmoc = | fluorenylmethoxycarbonyl |
| HOBT = | 1-hydroxybenzotriazole |
| Osu = | N-hydroxysuccinimide |
| TFA = | trifluoroacetic acid |
| THF = | tetrahydrofuran |

EXAMPLE 8

Cyclo[{4-($NH_2$—$C_2H_4$—NH—CO—O—)Pro}-DPhg-DTrp-Lys-Tyr(4-Bzl)-Phe]

a) Synthesis of Fmoc-Pro(4-OCO—NH—$CH_2$—$CH_2$—NH-Boc)-OH

L-hydroxyproline methylester hydrochloride is reacted with Fmoc-OSu in aqueous 1.0 N sodium carbonate/THF at room temperature. After completion of the reaction, Fmoc-Pro(4-OH)—OMe is isolated by precipitation. Fmoc-Pro(4-OH)—OMe is then added dropwise into a solution of trisphosgene (0.6 eq.) in THF to give a chlorocarbonate intermediate. After 1 h dimethylaminopyridine (1.0 eq.) and N-Boc-diaminoethane (6.0 eq.) are added and the reaction is stirred at room temperature. After completion of the reaction, the solvent is removed in vacuo and the resulting Fmoc-Pro(4-OCO—NH—$CH_2$—$CH_2$—NH-Boc)-OMe is extracted from a two phase system of ethyl acetate/0.1 M HCl to give crude product ($MH^+$=554) which is purified by crystallization from ethyl acetate. The methyl ester is then cleaved to the free acid by treatment with 1N NaOH in dioxane/water and the product Fmoc-Pro(4-OCO—NH—$CH_2$—$CH_2$—NH-Boc)-OH is purified on silica gel, $[(M+Na)]^+$=562).

b) H-Phe-Pro(4-OCO—NH—$CH_2$—$CH_2$—NH-Boc)-DPhg-DTrp(Boc)-Lys(Boc)-Tyr(Bzl)-OH

Commercially available Fmoc-Tyr(Bzl)-O—$CH_2$-Ph(3-$OCH_3$)—O—$CH_2$-Polystyrene resin (SASRIN-resin, 2.4 mM) is used as starting material and carried through a standard protocol consisting of repetitive cycles of Nα-deprotection (Piperidine/DMF, 2:8), repeated washings with DMF and coupling (DIPCl: 4.8 mM/HOBT: 6 mM, DMF). The following amino acid-derivatives are sequentially coupled: Fmoc-Lys(Boc)-OH, Fmoc-DTrp(Boc)-OH, Fmoc-DPhg-OH, Fmoc-Pro(4-OCO—NH—$CH_2$—$CH_2$—NH-Boc)-OH, Fmoc-Phe-OH. Couplings (2 eq. amino acids) are continued or repeated until completion, i.e. until complete disappearance of residual amino groups which is monitored by a negative 'Kaiser' Ninhydrin test. Before cleavage of the completely assembled protected linear peptide from its resin support the Nα-Fmoc protection from the last residue is removed.

c) H-Phe-Pro(4-OCO—NH—$CH_2$—$CH_2$—NH-Boc)-DPhg-DTrp(Boc)-Lys(Boc)-Tyr(Bzl)-OH

After washings with $CH_2Cl_2$, the peptide-resin is transferred into a column or a stirred suction filter and the peptide fragment is cleaved and eluted with a short treatment with 2% TFA in $CH_2Cl_2$ within 1 h. The eluate is immediately neutralized with a saturated $NaHCO_3$ solution. The organic solution is separated and evaporated and the side chain protected precursor ($MH^+$=1366) is cyclized without further purification.

d) cyclo[-Pro(4-OCO—NH—$CH_2CH_2$—$NH_2$)-DPhg-DTrp-Lys-Tyr(Bzl)-Phe-], trifluoroacetate The above linear fragment is dissolved in DMF (4 mM), cooled to minus 5° C. and treated with 2 eq. DIPEA then 1.5 eq. of DPPA and stirred until completion (ca. 20 h) at 0-4° C. The solvent was almost completely removed in vacuo; the concentrate is diluted with ethyl acetate, washed with $NaHCO_3$, water, dried and evaporated in vacuo.

For deprotection the residue is dissolved at 0° C. in TFA/$H_2O$ 95:5 (ca. 50 mM) and stirred in the cold for 30 min. The product is then precipitated with ether containing ca. 10 eq. HCl, filtered, washed with ether and dried. In order to completely decompose remaining Indole-N carbaminic acid the product is dissolved in 5% AcOH and lyophilized after 15 h at ca. 5° C. Preparative RP-HPLC is carried out on a C-18 10 μm STAGROMA column (5-25 cm) using a gradient of 0.5% TFA to 0.5% TFA in 70% acetonitrile. Fractions containing the pure title compound are combined, diluted with water and lyophilized. The lyophilisate is dissolved in water followed by precipitation with 10% $Na_2CO_3$ in water. The solid free base is filtered of, washed with water and dried in vacuum at room temperature. The resulting white powder is directly used for the different salts.

EXAMPLE 9

Cyclo[{4-($NH_2$—$C_2H_4$—NH—CO—O—)Pro}-DPhg-DTrp-Lys-Tyr(4-Bzl)-Phe] in Salt Form a. Acetate Conversion to the acetate salt form is carried out using an ion-exchange resin (e.g. AG 3-X4). MS (ESI): m/z 524.5 $[M+2H]^{2+}$
$[\alpha]_D^{20}$=−41.6°; c=0.56; AcOH 95%; T=20C, 589.3 nm b. Aspartate Conversion to the mono- or di-aspartate is obtained by reacting 1 equivalent of the compound of Example 8 with 1 or 2 equivalent of aspartic acid in a mixture of acetonitrile/water 1:3. The resulting mixture is frozen and lyophilized.

The di-aspartate may also be obtained by dissolving the compound of Example 8 in water/acetonitrile 4:1, filtering, loading on a an ion-exchange resin, e.g. BioRad AG4X4 column, and eluting with water/acetonitrile 4:1. The eluate is concentrated, frozen and lyophilized.

c. Benzoate

Conversion to the benzoate may be obtained by dissolving the compound of Example 8 with 2 equivalents of benzoic acid in a mixture of acetonitrile/water 1:2. The resulting mixture is frozen and lyophilized.

d. Pamoate 1 equivalent of the compound of Example 8 is dissolved together with 1 equivalent of embonic acid in a mixture of acetonitrile/THF/water 2:2:1. The resulting mixture is frozen and lyophilized.

EXAMPLE 10

Cyclo [{4-(DOTA-NH—$C_2H_4$—NH—CO—O—) Pro}-DPhg-DTrp-Lys-Tyr(4-Bzl)-Phe a) cyclo[-Pro(4-OCO—NH—$CH_2$—$CH_2$—$NH_2$)-DPhg-DTrp-Lys(Cbo)-Tyr(Bzl)-Phe-], trifluoroacetate The compound is synthesised in the same way like cyclo[-Pro(4-OCO—NH—$CH_2$—$CH_2$—$NH_2$)— DPhg-DTrp-Lys(Cbo)-Tyr(Bzl)-Phe-], trifluoroacetate by using Fmoc-Lys(Cbo)-OH instead of Fmoc-Lys(Boc)-OH.

b) 400 mg commercially available DOTAx$2H_2O$ (SYMAFEX-France) is dissolved in 20 ml water. After addition of 20 ml DMF, 170 mg cyclo[-Pro(4-OCO—NH—$CH_2$—$CH_2$—$NH_2$)-DPhg-DTrp-Lys(CBO)-Tyr(Bzl)-Phe-], together with 190 mg DCCl and 60 mg N-hydroxysuccinimide are added. The resulting suspension is kept at room temperature for 72 hours. After filtration, the solvent is removed under reduced pressure and the remaining crude is purified on silica gel (DCM/MeOH/HOAc$_{50\%}$ 8/2/0.25->7/3/1 as mobile phase).

c) For deprotection the above DOTA—conjugate is treated with 5 ml trifluoroacetic acid/thioanisole (9/1) for two hours at room temperature. After that the solution is poured into a mixture of 100 ml diethylether+5 ml 3N HCl/diethylether and the resulting precipitate ias isolated by filtration. Purification is performed on silica gel using DCM/MeOH/HOAc$_{50\%}$ 7/4/2->7/5/4 as mobile phase. Analytically pure endproduct is obtained after a desalting step using a 0.1% TFA to 0.1% TFA in 90% $CH_3CN$ gradient on a $R_{18}$—HPLC column (Spherisorb 250×4.6 mm). MH+: 1434.7

Compounds of formula III, e.g. Compound B, in free form or in the form of pharmaceutically acceptable salts and complexes exhibits valuable pharmacological properties as indicated in in vitro and in vivo tests and is therefore indicated for therapy.

More particularly, compounds of formula III, e.g. Compound B, exhibit an interesting binding profile for human somatostatin receptors (hsst). 5 somatostatin receptor subtypes, sst1, sst2, sst3, sst4 and sst5 have been cloned and characterized. hsst1, hsst2 and hsst3 and their sequences have been disclosed by Y. Yamada et al. in Proc. Nat. Acad. Sci., 89, 251-255 (1992). hsst4 and its sequence have been disclosed by L. Rohrer et al. in Proc. Acad. Sci., 90, 4196-4200 (1993). hsst5 and its sequence have been described by R. Panetta et al. in Mol. Pharmacol. 45, 417-427, 1993.

The binding assays may be carried out as disclosed hereunder using membranes from cell lines expressing selectively and stably hsst1, hsst2, hsst3, hsst4 or hsst5, e.g. CHO or COS cells.

Membranes are prepared according to known methods, e.g. as disclosed by C. Bruns et al. in Biochem. J., 1990, 65, page 39-44. Membranes prepared from hsst selective cell lines, e.g. CHO or COS cells stably expressing hsst1 or hsst2 or hsst3 or hsst4 or hsst5 are incubated in triplicate in a total volume of 300 μl at 22° C. for 30 min with increasing concentrations of [$^{125}$I-Tyr$^{11}$]-SRIF-14 in 10 mmol/l Hepes buffer (pH 7.6) containing 0.5% BSA. The incubation is terminated by rapid filtration and the filters are counted in a counter. Specific binding is total binding minus non-specific binding in the presence of 1 μmol/l somatostatin-14. The experiments are carried out in triplicate. The affinity constant ($K_D$) and number of binding sites are calculated using appropriate statistics and graphical programs.

Compounds of formula III, e.g. Compound B, have no significant binding affinity in the above binding assays towards hsst1, hsst2 and hsst4, a low binding affinity towards hsst3 and a good binding affinity towards hsst5 expressed as an $IC_{50}$ value in the nMolar range ($IC_{50}$=concentration for half-maximal inhibition in a competition binding assay using [$^{125}$I-Tyr$^{11}$]-SRIF-14 as specific radioligand).

| | $IC_{50}$ | | | | |
|---|---|---|---|---|---|
| | hsst1 | hsst2 | hsst3 | hsst4 | hsst5 |
| Compound B | >1000 | >1000 | 22 nM | 840 nM | 0.53 nM |

Compounds of formula III, e.g. Compound B, show GH-release inhibiting activity as indicated by the inhibition of GH release in vitro from cultured pituitary cells. For example, anterior pituitary glands from adult male rats are cut into small pieces and dispersed using 0.1% trypsin in 20 mM HEPES buffer. The dispersed cells are cultured for four days in MEM (Gibco) supplemented with 5% fetal calf serum, 5% horse serum, 1 mM $NaHCO_3$, 2.5 nM dexamethasone, 2.5 mg/ml insulin and 20 U/ml Pen/Strep. On the day of the experiment the attached cells are washed two times with Krebs-Ringer medium buffered with 20 mM HEPES and supplemented with 5 mM glucose and 0.2% BSA. Subsequently the cells are incubated for three hours with Compound B in the presence of 3×10$^{-10}$ M growth hormone releasing factor. The amount of growth hormone released into the medium is measured by RIA.

Compounds of formula III, e.g. Compound B, inhibit the release of growth hormone (GH) in rats. Compound B is administered s.c. to anaesthetized rats. Blood is collected after decapitation 1 h after administration of the compound. The duration of action is estimated on the basis of the inhibition of basal GH secretion 6 h after drug treatment. Hormone levels are measured by RIA 1 h and 6 h after treatment. The $ID_{50}$-value for the inhibition of the hormone secretion is determined graphically (log-probit) for each experiment and the resulting values are averaged logarithmically. In this in vivo model Compound B inhibits growth hormone release.

Compounds of formula III, e.g. Compound B, are also useful in the treatment of tumors which are hsst3 and/or hsst5 receptor positive, as indicated in proliferation tests with various cancer cell lines bearing hsst3 and/or hsst5.

Compounds of formula III, e.g. Compound B, are accordingly useful for the prevention or treatment of disorders with an aetiology comprising or associated with the presence or activation of hsst3 and/or hsst5, e.g. disorders or diseases associated with excess GH-secretion e.g. in the treatment of acromegaly or for the treatment of malignant cell proliferative diseases, e.g. cancer tumors bearing hsst3 and/or hsst5, e.g. as disclosed hereunder for the complexed conjugated Compound B.

For all the above indications the required dosage will of course vary depending upon, for example, the host, the mode of administration and the severity of the condition to be treated. In general, however, satisfactory results are obtained by administration in the order of from 1 µg to 0.7 mg/kg/day of compound of formula III, e.g. Compound B. An indicated daily dosage for patients is in the range from about 2 µg to about 50 mg, preferably about 0.01 to about 40 mg, e.g. about 0.01 to about 3 mg s.c. of the compound conveniently administered in divided doses up to 3 times a day in unit dosage form containing for example from about 0.5 µg to about 25 mg, e.g. from about 2 µg to 20 mg, for example from 2 µg to 1.5 mg of compound of formula III, e.g. Compound B.

The compounds of formula II, e.g. Compound B may be administered in free form or in pharmaceutically acceptable salt form or complexes. Such salts and complexes may be prepared in conventional manner and exhibit the same order of activity as the free compound. The present invention also provides a pharmaceutical composition comprising a compound of formula III, e.g. Compound B, in free base form or in pharmaceutically acceptable salt form or complex form, together with one or more pharmaceutically acceptable diluent or carrier. Such compositions may be formulated in conventional manner. The compounds of formula II, e.g. Compound B may also be administered in sustained release form, e.g. in the form of implants, microcapsules, microspheres or nanospheres comprising e.g. a biodegradable polymer or copolymer, in the form of a liposomal formulation, or in the form of an autogel, e.g. a solid or semi-solid composition capable of forming a gel after interaction with patient's body fluids.

The compounds of formula III, e.g. Compound B, or a pharmaceutically acceptable salt or complex thereof may be administered by any conventional route, for example parenterally e.g. in form of injectable solutions or suspensions (including e.g. the sustained release form as indicated above), orally using a conventional absorption enhancer, in a nasal or a suppository form or topically, e.g. in the form of an ophthalmic liquid, gel, oinment or suspension preparation, e.g a liposomal, microsphere or nanosphere formulation, e.g. for instillation or subconjunctival or intra- or peri-ocular injections.

In accordance with the foregoing the present invention further provides.

1. a compound of formula III, e.g. Compound B, or a pharmaceutically acceptable salt or complex thereof for use as a pharmaceutical:
2. A method of preventing or treating diseases or disorders as herein indicated in a subject in need of such treatment, which method comprises administering to said subject an effective amount of a compound of formula III, e.g. Compound B, or a pharmaceutically acceptable salt or complex thereof; or
3. a compound of formula III, e.g. Compound B, or a pharmaceutically acceptable salt or complex thereof for use in the preparation of a pharmaceutical composition for use in any method as defined under 2. above.

A conjugated compound of formula III, e.g. Compound B, or a pharmaceutically acceptable salt thereof is useful either as an imaging agent, e.g. visualisation of hsst3 and/or hsst5 receptor positive tissues and cells e.g. hsst3 and/or hsst5 receptor positive tumors and metastases, inflammatory or autoimmune disorders exhibiting somatostatin receptors, tuberculosis or organ rejection after transplantation, when complexed with a detectable element, e.g. a γ- or positron-emitting nuclide, a fluorescent metal ion or a paramagnetic ion, e.g. $^{111}$In, $^{161}$Tb, $^{177}$Lu, $^{86}$Y, $^{68}$Ga Eu$^{3+}$, Gd$^{3+}$, Fe$^{3+}$, Mn$^{2+}$ or Cr$^{2+}$, or as a radiopharmaceutical for the treatment in vivo of hsst3 and/or hsst5 receptor positive tumors and metastases, rheumatoid arthritis and severe inflammation conditions when complexed with an α- or β-emitting nuclide or a nuclide with Auger-e$^-$-cascades, e.g. $^{90}$Y, $^{161}$Tb, $^{177}$Lu, $^{211}$At, $^{213}$Bi or $^{201}$Tl, as indicated by standard tests.

In particular, it is observed that the conjugated Compound A binds to somatostatin receptors with pKi values of from about 8 to 10. Compound of Example 10 complexed with e.g. $^{111}$In, $^{88}$Y, $^{90}$Y or $^{177}$Lu binds in the nM range to the respective sst sub-types in accordance with the binding profile of Compound B.

The affinity of a conjugated compound of formula III, e.g. conjugated Compound B, and its complexes for hsst3 and/or hsst5 receptors can also be shown by in vivo testing, according to standard test methods, e.g. as disclosed in GB-A-2,225,579. For example the compound of Example 10 complexed with e.g. $^{111}$In, $^{88}$Y, $^{90}$Y or $^{177}$Lu, gives a significant tumor accumulation 4 hours after injection into mice or rats bearing an exocrine pancreatic tumor expressing hsst5 receptors.

After administration of a conjugated compound of formula III, e.g. conjugated Compound B, in complexed form, e.g. radiolabelled with $^{111}$In, $^{177}$Lu, $^{86}$Y or $^{161}$Tb, at a dosage of from 1 to 5 µg/kg labelled with 0.1 to 5 mCi radionuclide, preferably 0.1 to 2 mCi, the tumor site becomes detectable.

The conjugated compound of formula III, e.g. conjugated Compound B, when radiolabelled with an α- or β-emitting radionuclide or a nuclide with Auger-e$^-$-cascades exhibits an antiproliferative and/or cytotoxic effect on tumor cells bearing hsst3 and/or hsst5 receptors, e.g. as indicated in nude mice tests.

Nude mice are inoculated with hsst5 bearing tumor cells. When tumors have reached a volume of 1 to 2 cm$^3$ animals are randomized into control and treatment groups. A conjugated compound of formula III, e.g. conjugated Compound B in complexed form is administered by i.p. or i.v. injections. Doses up to 40 mCi/kg are given per mouse. The size of the tumors is determined with a caliper as disclosed above. For statistical calculations Students t-test is applied. In this test, transient tumor shrinkage is observed after one week and tumor growth is delayed for two weeks upon a single application of the compound of Example 10 complexed with $^{90}$Y or $^{177}$Lu. In contrast the control groups showed continuous tumor growth with a volume doubling time of about seven days.

Accordingly, in a series of specific or alternative embodiments, the present invention also provides:

4. Use of a conjugated compound of formula III, e.g. conjugated Compound B, complexed with a detectable element for in vivo detection of hsst3 and/or hsst5 positive cells and tissues, e.g. hsst3 or hsst5 positive tumors and metastasis, in a subject and recording the localisation of the receptors targeted by said complex;
5. A method for in vivo detection of hsst3 and/or hsst5 positive tissues and cells, e.g. hsst3 or hsst5 positive tumors and metastasis, in a subject comprising administering to said subject a conjugated compound of formula III, e.g. conjugated Compound B, complexed with a detectable element, or a pharmaceutically acceptable salt form, and recording the localization of the receptors targeted by said complex.

The conjugated compound of formula III, e.g. conjugated Compound B, in complexed form for use as an imaging agent may be administered e.g. intravenously, e.g. in the form of injectable solutions or suspensions, preferably in the form of a single injection. The radiolabelling may preferably be performed shortly before administration to a subject.

In animals an indicated dosage range may be from 0.01 to 1 µg/kg of a conjugated compound of formula III, e.g. conjugated Compound B, complexed with 0.02 to 0.5 mCi γ-emitting radionuclide. In larger mammals, for example humans, an indicated dosage range may be from 1 to 100 µg/m$^2$ conjugated Compound B complexed e.g. with 1 to 100 mCi/m$^2$ detectable element, e.g. $^{111}$In, $^{86}$Y or $^{177}$Lu.

6. Use of a conjugated compound of formula III, e.g. conjugated Compound B, complexed with an α- or β-emitting nuclide or a nuclide with Auger-e$^-$-cascades, for in vivo treatment of hsst3 and/or hsst5 positive tumors and metastases.

7. A method for in vivo treatment of hsst3 and/or hsst5 positive tumors and metastases, e.g. for treating invasiveness of such tumors or symptoms associated with such tumor growth, in a subject in need of such treatment which comprises administering to said subject a therapeutically effective amount of a conjugated compound of formula III, e.g. conjugated Compound B, complexed with an α- or β-emitting nuclide or a nuclide with Auger-e⁻-cascades.

8. Use of a conjugated compound of formula III, e.g. conjugated Compound B, or a pharmaceutically acceptable salt thereof in the manufacture of an imaging agent or a radiopharmaceutical composition.

Dosages employed in practising the radiotherapeutic use of the present invention will of course vary depending e.g. on the particular condition to be treated, for example the known radiotoxicity to normal organs expressing hsst5, the volume of the tumor and the therapy desired. In general, the dose is calculated on the basis of pharmacokinetik and radioactivity distribution data obtained in to healthy organs and based on the observed target uptake. A β-emitting complex of a conjugated compound of formula III, e.g. conjugated Compound B, may be administered repeatedly e.g. over a period of 1 to 3 months.

In animals an indicated dosage range may be from 20 to 100 μg/kg conjugated compound of formula III, e.g. conjugated Compound B, complexed with 15 to 70 mCi of an α- or β-emitting nuclide or a nuclide with Auger-e⁻-cascades, e.g. $^{90}$Y, $^{177}$Lu or $^{161}$Tb. In larger mammals, for example humans, an indicated dosage range may be from 1 to 100 μg/m$^2$ conjugated compound of formula II, e.g. conjugated Compound B, complexed e.g. with 1 to 100 mCi/m$^2$ of an α- or β-emitting nuclide or a nuclide with Auger-e⁻-cascades, e.g. $^{90}$Y, $^{177}$Lu or $^{161}$Tb.

A conjugated compound of formula III, e.g. conjugated Compound B, in complexed form for use as a radiotherapeutic agent may be administered by any conventional route, e.g. intravenously, e.g. in the form of injectable solutions. It may also be administered advantageously by infusion, e.g. an infusion over 15 to 60 min. Depending on the site of the tumor, it may be administered as close as possible to the tumor site, e.g. by means of a catheter. The present invention also provides a pharmaceutical composition comprising a conjugated compound of formula III, e.g. conjugated Compound B, in free base form or in pharmaceutically acceptable salt form or complexed with a detectable or radiotherapeutic agent, together with one or more pharmaceutically acceptable diluent or carrier.

A compound of formula III or a conjugated compound of formula III, e.g. Compound B or the conjugated Compound B, in complexed form may be suitable for imaging or treating hsst3 and/or hsst5 expressing or accumulating such as pituitary tumors, e.g. adenomas or prolactinomas, gastro-enteropancreatic tumors, carcinoids, central nervous system, breast, prostatic (including advanced hormone-refractory prostate cancer), ovarian or colonic tumours, small cell lung cancer, malignant bowel obstruction, paragangliomas, kidney cancer, skin cancer, neuroblastomas, pheochromocytomas, medullary thyroid carcinomas, myelomas, iymphomas, Hodgkins and non-Hodgkins lymphomas, bone tumours and metastases thereof, as well as autoimmune or inflammatory disorders, e.g. rheumatoid arthritis, Graves disease or other inflammatory eye diseases.

According to a further aspect of the invention, there is provided a pharmaceutical composition comprising a conjugated compound of formula III, e.g. conjugated Compound B, or a complex thereof together with one or more pharmaceutically acceptable carriers or diluents therefor. Such compositions may be manufactured in conventional manner and may be presented, e.g. for imaging, in form of a kit comprising two separate dosages, one being the radionuclide and the other the conjugated compound of formula III, e.g. conjugated Compound B, with instructions for mixing them. For radiotherapy, the conjugated compound of formula III, e.g. conjugated Compound B, in complexed form may preferably be in the form of a hot liquid formulation.

A compound of formula III optionally conjugated, e.g. Compound B or a conjugated Compound B, in complexed form may be administered as the sole active ingredient or in conjuction with, e.g. as an adjuvant to, other drugs. For example, a compound of formula III, e.g. Compound B, may be used in combination with an immunosuppressive agent, e.g. a calcineurin inhibitor, e.g. cyclosporin A, isa Tx247 or FK 506; a mTOR inhibitor, e.g. rapamycin, CCI779, ABT578 or 40-O-(2-hydroxyethyl)-rapamycin; an ascomycin having immunosuppressive properties, e.g. ABT-281, ASM981, etc.; corticosteroids; cyclo-phosphamide; azathioprene; methotrexate; leflunomide; mizoribine; mycophenolic acid or a salt thereof, e.g. Myfortic$^R$; mycophenolate mofetil; 15-deoxyspergualine or an immunosuppressive homologue, analogue or derivative thereof; a S1P receptor agonist, e.g. FTY720; immunosuppressive monoclonal antibodies, e.g., monoclonal antibodies to leukocyte receptors, e.g., MHC, CD2, CD3, CD4, CD7, CD8, CD25, CD28, CD40, CD45, CD58, CD80, CD86 or to their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof e.g. LEA29Y; adhesion molecule inhibitors, e.g. LFA-1 antagonists, ICAM-1 or -3 antagonists, VCAM-4 antagonists or VLA-4 antagonists. A compound of formula III, e.g. Compound B may also be used in combination with an anti-inflammatory agent, a GH secretagogue receptor modulating agent, e.g. ghrelin or hexarelin, a GH receptor antagonist, e.g. pegvisomant, A compound of formula III optionally conjugated, e.g. Compound B or a conjugated Compound B, in complexed form may also be used in combination with an antiproliferative agent, e.g. a chemotherapeutic drug, e.g. paclitaxel, gemcitabine, cisplatinum, doxorubicin, 5-fluorouracil or taxol, a hormonal agent or antagonist, e.g. an anti-androgen or mitoxantrone (especially in the case of prostate cancer), or an antiestrogen, like letrozole (especially in the case of breast cancer), an antimetabolite, a plant alkaloid, a biological response modifier, preferably a lymphokine or interferons, an inhibitor of protein tyrosine kinase and/or serine/threonine kinase, or an agent with other or unknown mechanism of action, e.g. any epothilone or epothilone derivative, or a mTOR inhibitor, e.g. as indicated above.

Where a compound of formula III optionally conjugated, e.g. Compound B or a conjugated Compound B, in complexed form is administered in conjunction with another drug, dosages of the co-administered drug will of course vary depending on the type of co-drug employed, on the specific drug employed, on the condition to be treated, and so forth. The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

In accordance with the foregoing the present invention provides in a yet further aspect:

9. A pharmaceutical combination comprising a) a first agent which is a compound of formula III optionally conjugated, e.g. Compound B or a conjugated Compound B, in complexed form and b) a co-agent, e.g. as defined above.

10. A method as defined above comprising co-administration, e.g. concomitantly or in sequence, of a therapeutically effective amount of a compound of formula III optionally conjugated, e.g. Compound B or a conjugated Compound B in complexed form, and a second drug substance, said second drug substance being, e.g. as indicated above.

The invention claimed is:

1. A liquid formulation for parenteral administration comprising tartaric acid and a somatostatin of formula II

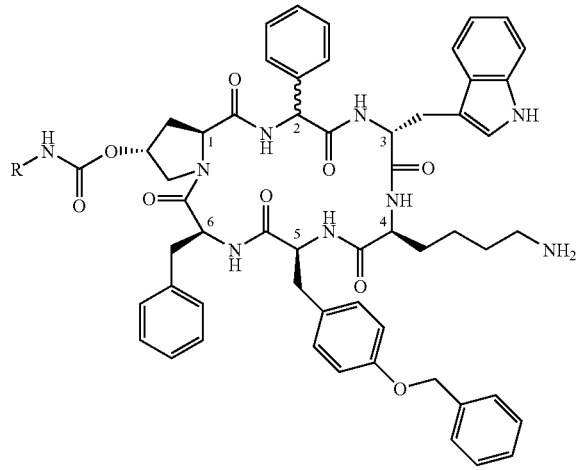

II wherein the configuration at C-2 is (R) or (S) or a mixture thereof, and wherein R is $NR_1 R_2$—$C_{2-6}$ alkylene or guanidine-$C_{2-6}$ alkylene, and each of $R_1$ $R_2$ independently is H or $C_{1-4}$ alkyl, in free form, salt form, or protected form.

2. The liquid formulation according to claim 1 wherein the compound of the somatostatin is in aspartate di-salt form.

3. The liquid formulation according to claim 1 wherein the formulation is adjusted to a pH of about 4 to about 4.5.

4. The liquid formulation according to claim 1 wherein the somatostatin is cyclo[{4-($NH_2$—$C_2H_4$—NH—CO—O)Pro}-Phg-DTrp-Lys-Tyr(4-Bzl)-Phe] or a pharmaceutically acceptable salt thereof.

5. The liquid formulation according to claim 2 wherein the somatostatin is cyclo[{4-($NH_2$—$C_2H_4$—NH—CO—O)Pro}-Phg-DTrp-Lys-Tyr(4Bzl)-Phe] or a pharmaceutically acceptable salt thereof.

* * * * *

UNITED STATES PATENT AND TRADEMARK OFFICE
CERTIFICATE OF CORRECTION

PATENT NO. : 8,299,209 B2  
APPLICATION NO. : 12/359527  
DATED : October 30, 2012  
INVENTOR(S) : Olivier Lambert and Katrin Moser Page 1 of 1

It is certified that error appears in the above-identified patent and that said Letters Patent is hereby corrected as shown below:

Title Page, Item (30) entitled Foreign Application Priority Data, to read

--Jun 24, 2003 (GB).................................0314695.8  
Oct 30, 2003 (GB)................................0325388.7--

Signed and Sealed this  
Twenty-fifth Day of December, 2012

David J. Kappos  
*Director of the United States Patent and Trademark Office*